United States Patent
Gottimukkala et al.

(10) Patent No.: US 9,953,130 B2
(45) Date of Patent: Apr. 24, 2018

(54) SYSTEMS AND METHODS FOR DETECTING STRUCTURAL VARIANTS

(71) Applicant: LIFE TECHNOLOGIES CORPORATION, Carlsbad, CA (US)

(72) Inventors: Rajesh Gottimukkala, Foster City, CA (US); Fiona Hyland, San Mateo, CA (US); Sowmi Utiramerur, Cupertino, CA (US); Jeoffrey Schageman, Austin, TX (US); Susan Magdaleno, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 517 days.

(21) Appl. No.: 14/503,461

(22) Filed: Oct. 1, 2014

(65) Prior Publication Data

US 2015/0094212 A1    Apr. 2, 2015

Related U.S. Application Data

(60) Provisional application No. 61/885,082, filed on Oct. 1, 2013, provisional application No. 61/919,306, filed on Dec. 20, 2013.

(51) Int. Cl.
*C12Q 1/68* (2006.01)
*G06F 19/18* (2011.01)

(52) U.S. Cl.
CPC .......... *G06F 19/18* (2013.01); *C12Q 1/6858* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 2010/0062450 A1* | 3/2010 | Arber | C12Q 1/6886 435/7.1 |
| 2013/0110410 A1 | 5/2013 | Hong et al. | |
| 2013/0210645 A1* | 8/2013 | Volgelstein | C12Q 1/6886 506/4 |

FOREIGN PATENT DOCUMENTS

| WO | WO-2011/017596 | 2/2011 |
|---|---|---|
| WO | 2011/073665 | 6/2011 |
| WO | WO 2013/081755 | 6/2013 |

OTHER PUBLICATIONS

European Office action dated Mar. 5, 2018 for application 14789671.6. (Year: 2018).*
Caye, A. et al., "Breakpoint-specific multiplex polymerase chain reaction allows the detection of IKZF1 intragenic deletions and minimal residual disease monitoring in B-cell precursor acute lymphoblastic leukemia", *Haematologica*, vol. 98 (4), Oct. 12, 2012, 597-601.

(Continued)

Primary Examiner — Samuel C Woolwine

(57) ABSTRACT

Systems and method for identifying long deletions can obtain sequencing information for a plurality of amplicons in and around a potential region from a nucleic acid sample. The sequencing information can include a plurality of reads that can be mapped to a reference sequence. Using information, such as where reads map to a reference sequence and relative abundance of reads for the amplicons, structural variants can be identified and a determination can be made if the nucleic acid sample is homozygous or heterozygous for the structural variant.

15 Claims, 8 Drawing Sheets

(56) References Cited

OTHER PUBLICATIONS

Okoniewski, M. et al., "Precise breakpoint localization of large genomic deletions using PacBio and Illumina next-generation sequencers", *Biotechniques*, vol. 54 (2), Feb. 1, 2013, 98-100.

Patel, A. et al., "Amplification and thrifty single-molecule sequencing of recurrent somatic structural variations", *Genome Research*, vol. 24, Dec. 4, 2013, 318-328.

PCT/US2014/058517, International Search Report and Written Opinion dated Jan. 21, 2015, 11 Pages.

PCT/US2014/058517, International Preliminary Report on Patentability dated Apr. 14, 2016, 7 pp.

Edgren, H et al., "Identification of fusion genes in breast cancer by paired-end RNA-sequencing" *Genome Biology, Biomed Central, Ltd.*, London, GB, vol. 12, No. 1, Jan. 19, 2011, 14 pp.

\* cited by examiner

SYSTEMS AND METHODS FOR DETECTING STRUCTURAL VARIANTS

FIELD

The present disclosure generally relates to the field of nucleic acid sequencing including systems and methods for detecting structural variants.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible. These goals can be reached through the use of sequencing platforms and methods that provide sample preparation for samples of significant complexity, sequencing larger numbers of samples in parallel (for example through use of barcodes and multiplex analysis), and/or processing high volumes of information efficiently and completing the analysis in a timely manner. Various methods, such as, for example, sequencing by synthesis, sequencing by hybridization, and sequencing by ligation are evolving to meet these challenges.

Ultra-high throughput nucleic acid sequencing systems incorporating NGS technologies typically produce a large number of short sequence reads. Sequence processing methods should desirably assemble and/or map a large number of reads quickly and efficiently, such as to minimize use of computational resources. For example, data arising from sequencing of a mammalian genome can result in tens or hundreds of millions of reads that typically need to be assembled before they can be further analyzed to determine their biological, diagnostic and/or therapeutic relevance.

Exemplary applications of NGS technologies include, but are not limited to: genomic variant detection, such as insertions/deletions, copy number variations, single nucleotide polymorphisms, etc., genomic resequencing, gene expression analysis and genomic profiling.

Structural variants, such as large scale deletions, insertions, inversions, genomic rearrangements, gene fusions, and the like, can be associated with various genetic disorders and cancers. For example, two large deletions in the CFTR gene, CFTRdele2,3 and CFTRdele22,23, have been identified in cystic fibrosis patients. Other structural variants can include gene fusions, where part of a first gene is spliced together with a part of a second gene, which can occur through chromosomal rearrangements, large deletions, partial gene duplications, and the like. Structural variants can be more difficult to detect than smaller sequence variations, such as single nucleotide polymorphisms. Since the size of the structural variant can be many times the read length used for sequencing, single reads may not span the entire structural variation.

From the foregoing it will be appreciated that a need exists for systems and methods that can detect large deletions using nucleic acid sequencing data.

DRAWINGS

For a more complete understanding of the principles disclosed herein, and the advantages thereof, reference is now made to the following descriptions taken in conjunction with the accompanying drawings, in which.

Figure 1:
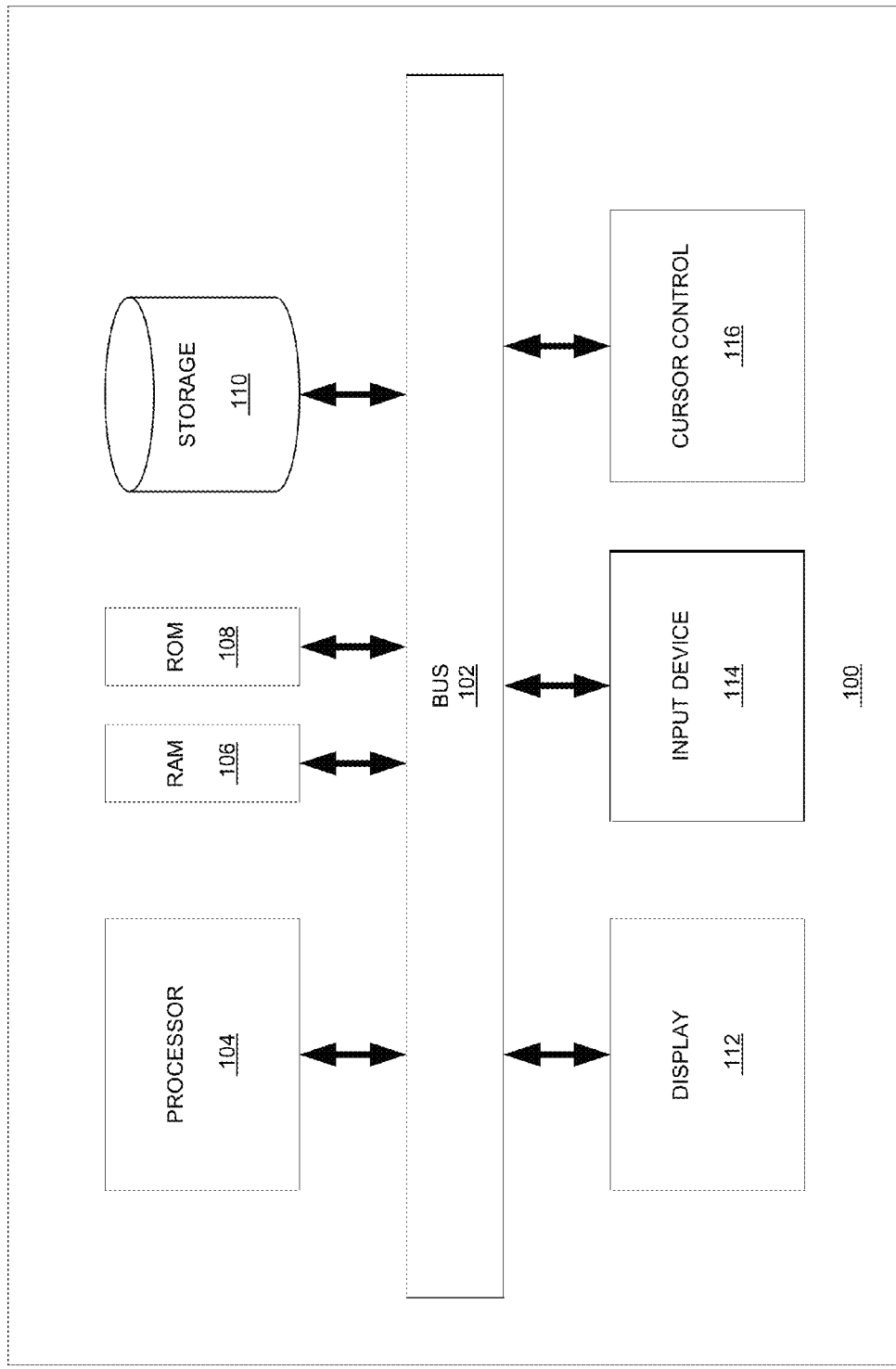
FIG. 1 is a block diagram that illustrates an exemplary computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for detecting low frequency variants are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

In various embodiments, a "system" sets forth a set of components, real or abstract, comprising a whole where each component interacts with or is related to at least one other component within the whole.

In various embodiments, a "biomolecule" may refer to any molecule that is produced by a biological organism, including large polymeric molecules such as proteins, polysaccharides, lipids, and nucleic acids (DNA and RNA) as well as small molecules such as primary metabolites, secondary metabolites, and other natural products.

In various embodiments, the phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Personal Genome Machine (PGM) and Proton of Life Technologies Corp. provides massively parallel sequencing with enhanced accuracy. The PGM and Proton Systems and associated workflows, protocols, chemistries, etc. are described in more detail in U.S. Patent Application Publication No. 2009/0127589 and No. 2009/0026082, the entirety of each of these applications being incorporated herein by reference.

In various embodiments, the phrase "sequencing run" refers to any step or portion of a sequencing experiment performed to determine some information relating to at least one biomolecule (e.g., nucleic acid molecule).

In various embodiments, the phrase "base space" refers to a representation of the sequence of nucleotides. The phrase "flow space" refers to a representation of the incorporation event or non-incorporation event for a particular nucleotide flow. For example, flow space can be a series of values representing a nucleotide incorporation events (such as a one, "1") or a non-incorporation event (such as a zero, "0") for that particular nucleotide flow. Nucleotide flows having a non-incorporation event can be referred to as empty flows, and nucleotide flows having a nucleotide incorporation event can be referred to as positive flows. It should be understood that zeros and ones are convenient representations of a non-incorporation event and a nucleotide incorporation event; however, any other symbol or designation could be used alternatively to represent and/or identify these events and non-events. In particular, when multiple nucleotides are incorporated at a given position, such as for a homopolymer stretch, the value can be proportional to the number of nucleotide incorporation events and thus the length of the homopolymer stretch.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems (such as Illumina HiSeq, MiSeq, and Genome Analyzer), hybridization-based systems, direct or indirect nucleotide identification systems, pyrosequencing (such as 454 Life Science GS FLX and GS Junior), ion- or pH-based detection systems (such as Ion Torrent), electronic signature-based systems (such as Oxford Nanopore GridION and MinION), etc.

In various embodiments, a "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

In various embodiments, a "structural variant" refers to a variation in the structure of a chromosome. Structural variants can include deletions, duplications, copy-number variants, insertions, gene fusions, inversions and translocations. Many of structural variants are associated with genetic diseases, however more are not.

Multiplex Amplification Methods:

In various embodiments, target nucleic acids generated by the amplification of multiple target-specific sequences from a population of nucleic acid molecules can be sequenced. In some embodiments, the amplification can include hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the amplified target sequences can be ligated to one or more adapters. In some embodiments, the adapters can include one or more nucleotide barcodes or tagging sequences. In some embodiments, the amplified target sequences once ligated to an adapter can undergo a nick translation reaction and/or further amplification to generate a library of adapter-ligated amplified target sequences. Exemplary methods of multiplex amplification are described in U.S. application Ser. No. 13/458,739 filed Nov. 12, 2012 and titled "Methods and Compositions for Multiplex PCR".

In various embodiments, the method of performing multiplex PCR amplification includes contacting a plurality of target-specific primer pairs having a forward and reverse primer, with a population of target sequences to form a plurality of template/primer duplexes; adding a DNA polymerase and a mixture of dNTPs to the plurality of template/primer duplexes for sufficient time and at sufficient temperature to extend either (or both) the forward or reverse primer in each target-specific primer pair via template-dependent synthesis thereby generating a plurality of extended primer product/template duplexes; denaturing the extended primer product/template duplexes; annealing to the extended primer product the complementary primer from the target-specific primer pair; and extending the annealed primer in the presence of a DNA polymerase and dNTPs to form a plurality of target-specific double-stranded nucleic acid molecules.

Computer-Implemented System

FIG. 1 is a block diagram that illustrates an exemplary computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

In various embodiments, the term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 2:
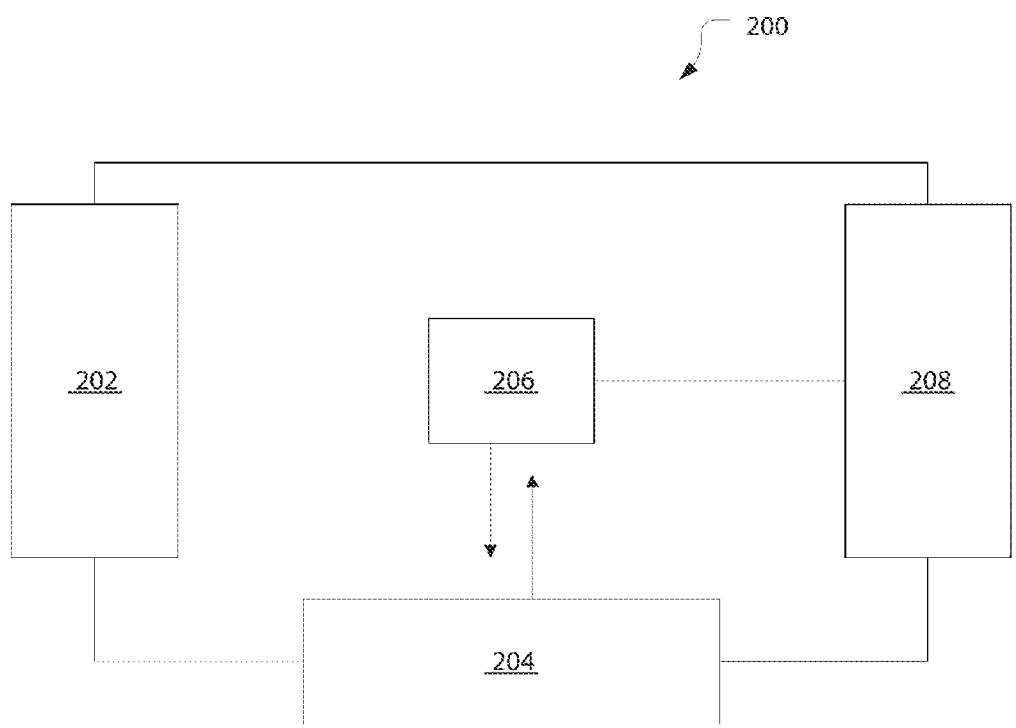
FIG. 2 is a schematic diagram of an exemplary system for reconstructing a nucleic acid sequence, in accordance with various embodiments.

Various embodiments of nucleic acid sequencing platforms, such as a nucleic acid sequencer, can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082 are incorporated herein by reference. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145, the entirety of which being incorporated herein by reference) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

System and Methods for Identifying Sequence Variation

Figure 3:
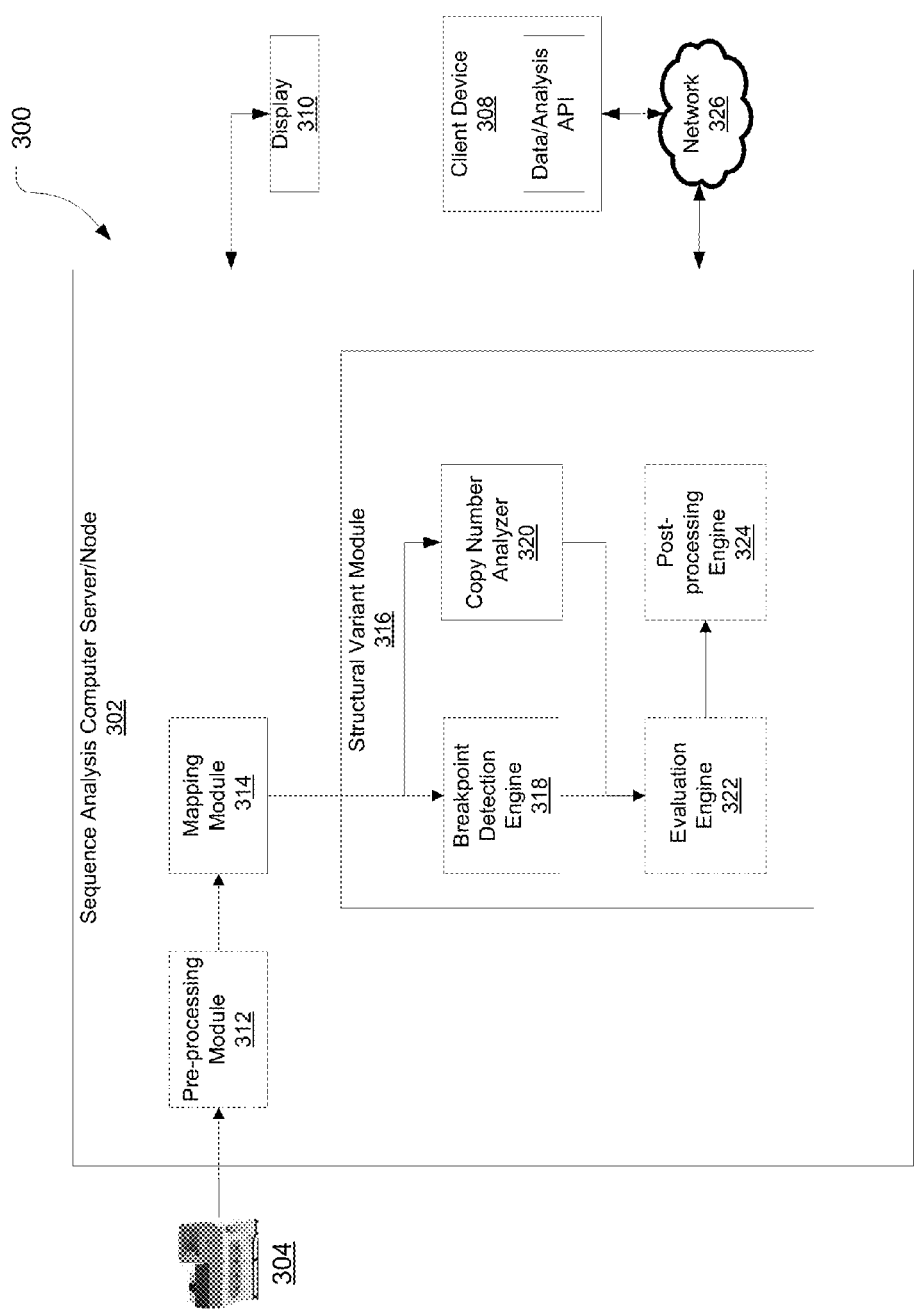
FIG. 3 is a schematic diagram of an exemplary genetic analysis system, in accordance with various embodiments.

FIG. 3 is a schematic diagram of a system for identifying variants, in accordance with various embodiments.

As depicted herein, variant analysis system 300 can include a nucleic acid sequence analysis device 304 (e.g., nucleic acid sequencer, real-time/digital/quantitative PCR instrument, microarray scanner, etc.), an analytics computing server/node/device 302, and a display 310 and/or a client device terminal 308.

In various embodiments, the analytics computing server/node/device 302 can be communicatively connected to the nucleic acid sequence analysis device 304, and client device terminal 308 via a network connection 326 that can be either a "hardwired" physical network connection (e.g., Internet, LAN, WAN, VPN, etc.) or a wireless network connection (e.g., Wi-Fi, WLAN, etc.).

In various embodiments, the analytics computing device/server/node 302 can be a workstation, mainframe computer, distributed computing node (such as, part of a "cloud computing" or distributed networking system), personal computer, mobile device, etc. In various embodiments, the nucleic acid sequence analysis device 304 can be a nucleic acid sequencer, real-time/digital/quantitative PCR instrument, microarray scanner, etc. It should be understood, however, that the nucleic acid sequence analysis device 304 can essentially be any type of instrument that can generate nucleic acid sequence data from samples obtained from an individual.

The analytics computing server/node/device 302 can be configured to host an optional pre-processing module 312, a mapping module 314, and a structural variant module 316.

Pre-processing module 312 can be configured to receive from the nucleic acid sequence analysis device 304 and perform processing steps, such as conversion from f space to base space, color space to base space, or from flow space to base space, determining call quality values, preparing the read data for use by the mapping module 314, and the like.

The mapping module 314 can be configured to align (i.e., map) a nucleic acid sequence read to a reference sequence. Generally, the length of the sequence read is substantially less than the length of the reference sequence. In reference sequence mapping/alignment, sequence reads are assembled against an existing backbone sequence (e.g., reference sequence, etc.) to build a sequence that is similar but not necessarily identical to the backbone sequence. Once a backbone sequence is found for an organism, comparative sequencing or re-sequencing can be used to characterize the genetic diversity within the organism's species or between closely related species. In various embodiments, the reference sequence can be a whole/partial genome, whole/partial exome, etc.

In various embodiments, the sequence read and reference sequence can be represented as a sequence of nucleotide base symbols in base space. In various embodiments, the sequence read and reference sequence can be represented as one or more colors in color space. In various embodiments, the sequence read and reference sequence can be represented as nucleotide base symbols with signal or numerical quantitation components in flow space.

In various embodiments, the alignment of the sequence fragment and reference sequence can include a limited number of mismatches between the bases that comprise the sequence fragment and the bases that comprise the reference sequence. Generally, the sequence fragment can be aligned to a portion of the reference sequence in order to minimize the number of mismatches between the sequence fragment and the reference sequence.

The structural variant module 316 can include a breakpoint detection engine 318, a copy number analyzer 320, an evaluation engine 322, and an optional post processing engine 324. In various embodiments, structural variant module 316 can be in communications with the mapping module 314. That is, structural variant module 316 can request and receive data and information (through, e.g., data streams, data files, text files, etc.) from mapping module 314.

The breakpoint detection engine 318 can be configured to receive mapped reads from the mapping module 314, and identify reads aligned to a breakpoint region. Additionally, the breakpoint detection engine 318 can align the reads from the breakpoint to a modified reference sequence. The modified reference sequence can contain a reference haplotype and a putative structural variant haplotype. The breakpoint detection engine 318 can identify the presence of the structural variant and the genotype (heterozygous or homozygous) based on the alignment of the reads to the modified reference sequence.

Copy number analyzer 320 can be configured to receive mapped reads from the mapping module 314. The copy number analyzer 320 can detect copy number variations based on changes in the coverage between the region with a copy number variation and regions without copy number variations. Exemplary methods of detecting copy number variations are described in U.S. Application No. 61/733,584, filed Mar. 6, 2013 and titled "SYSTEMS AND METHODS FOR DETERMINING COPY NUMBER VARIATION".

Evaluation engine 322 can be configured to receive evidence from the breakpoint detection engine 318 and the copy number analyzer 320. Based on the evidence received from the breakpoint detection engine 318 and the copy number analyzer 320, the evaluation engine can classify the variant and determine a confidence value.

Post processing engine 324 can be configured to receive the structural variants identified by the evaluation engine 318 and perform additional processing steps, such as filtering deletions, and formatting the read data for display on display 310 or use by client device 308.

Client device 308 can be a thin client or thick client computing device. In various embodiments, client terminal 308 can have a web browser (e.g., INTERNET EXPLORER™, FIREFOX™, SAFARI™, etc) that can be used to communicate information to and/or control the operation of the pre-processing module 312, mapping module 314, breakpoint detection engine 318, copy number analyzer 320, evaluation engine 322, and post processing engine 324 using a browser to control their function. For example, the client terminal 308 can be used to configure the operating parameters (e.g., match scoring parameters, annotations parameters, filtering parameters, data security and retention parameters, etc.) of the various modules, depending on the requirements of the particular application. Similarly, client terminal 308 can also be configure to display the results of the analysis performed by the structural variant module 316 and the nucleic acid sequencer 304.

It should be understood that the various data stores disclosed as part of system 300 can represent hardware-based storage devices (e.g., hard drive, flash memory, RAM, ROM, network attached storage, etc.) or instantiations of a database stored on a standalone or networked computing device(s).

It should also be appreciated that the various data stores and modules/engines shown as being part of the system 300 can be combined or collapsed into a single module/engine/data store, depending on the requirements of the particular application or system architecture. Moreover, in various embodiments, the system 300 can comprise additional modules, engines, components or data stores as needed by the particular application or system architecture.

In various embodiments, the system 300 can be configured to process the nucleic acid reads in color space. In various embodiments, system 300 can be configured to process the nucleic acid reads in base space. In various embodiments, system 300 can be configured to process the nucleic acid sequence reads in flow space. It should be understood, however, that the system 300 disclosed herein can process or analyze nucleic acid sequence data in any schema or format as long as the schema or format can convey the base identity and position of the nucleic acid sequence.

Figure 4:
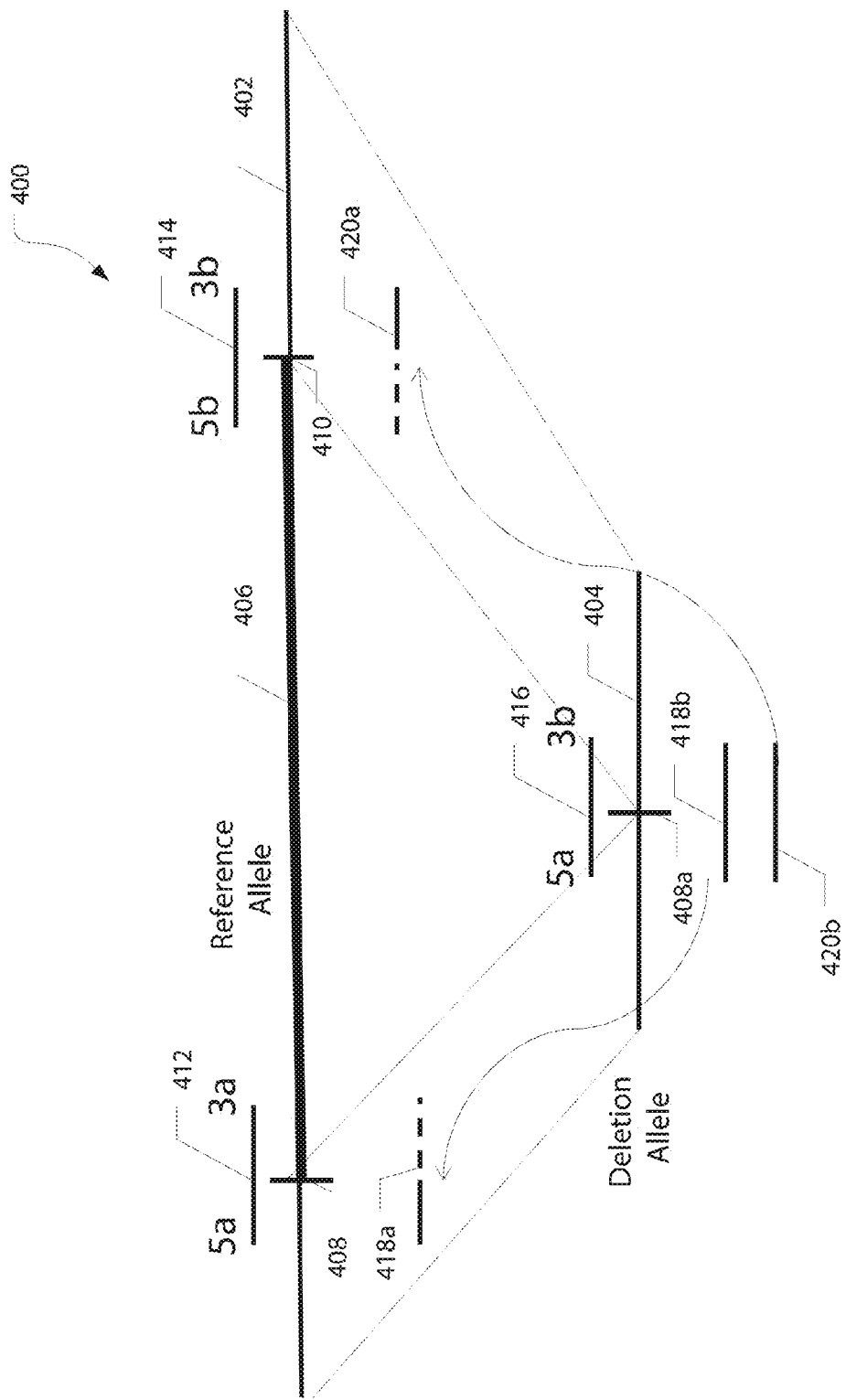
FIG. 4 is a diagram illustrating an exemplary deletion, in accordance with various embodiments.

FIG. 4 is a diagram showing an exemplary structural variant 400, specifically a deletion. Haplotype 402 can be a full length reference sequence. Haplotype 404 can contain the putative structural variant. In this case, region 406 is present in haplotype 402 but deleted in haplotype 404. Breakpoints 408 and 410 correspond to the edges of region 406 in haplotype 402, while in haplotype 404, the sequence outside of region 406 from breakpoint 408 and breakpoint 410 are adjacent at breakpoint 408a.

Regions 412 and 414 can correspond to amplicons generated from haplotype 402. These amplicons can be generated by amplifying a nucleic acid sample from an individual having the reference haplotype 402 using primer pair 5a and 3a and primer pair 5b and 3b. However, when amplifying a nucleic acid sample from an individual having the deletion haplotype 404 using primers 5a, 5b, 3a, and 3b, an amplicon corresponding to region 416 can be produced from primers 5a and 3b.

In an exemplary embodiment, amplicons generated from region 416 and primers 5a and 3b can be partially mapped at 418a and 420a to regions 412 and 414 when mapped against a reference sequence not including the deletion haplotype 404. However, when mapped against a modified reference containing both the reference haplotype 402 and the deletion haplotype 404, the amplicons can be mapped to region 416 at 418b and 420b.

In various embodiments, optimal positioning of the primers relative to the breakpoint can depend on read length of the sequencing system and the type of sample being analyzed. To minimize sequencing errors in both the forward and reverse directions, the break point can be located at approximately the midpoint between the two primers. Generally, the amplicon and sequence read can extend from the breakpoint in both directions to provide sufficient information to identify the sequence on each side of the breakpoint. For example, a read can extend at least 10 bases, at least 20 bases, or even at least 25 bases either side of the breakpoint. As such, the primers can be located at least far enough from the breakpoint to provide a sufficient read length between the primer and the breakpoint. Additionally, the primers should be located close enough to the break point for the expected read length to extend a sufficient distance past the break point. Further, the overall size of the amplicon can be limited by sample quality. For example, formalin-fixed paraffin embedded (FFPE) samples, such as for histological studies, tend to have partially degraded RNA and DNA. When working with partially degraded samples, the size of the amplicon can be limited to less than the average fragment length of the sample. For example, the amplicon may be limited to not greater than 150 bases, not greater than 140 bases, even not greater than 130 bases.

While FIG. 4 illustrates a deletion, it should be understood by those with skill in the art that the similar arrangements can be seen with other structural variations. For example, for an insertion, two primer pairs (5a-3a and 5b-3b) designed to amplify the regions around the breakpoints in the insertion haplotype can generate amplicons (5a-3b) mapped to the region around the breakpoint in the reference haplotype using one primer from each primer pair. In another example, an inversion can be detected using two primer pairs (5a-3a and 5b-3b) designed to amplify the regions around the breakpoints in the reference haplotype. In the inversion, two groups of amplicons (5a-5b and 3a-3b) can be generated by taking one primer from each pair. In yet another example, a gene fusion could be similar to the deletion except that the 5a-3a primers could amplify a breakpoint region in a first gene and the 5b-3b primers could amplify a breakpoint region in a second gene. With the gene fusion, an amplicon 5a-3b can be generated containing portions of both the first and second genes. In a translocation, where a segment of DNA is moved from one location to another, two primer pairs (5a-3a and 5b-3b) flanking the segment in the reference haplotype and a primer pair (5c-3c) flanking the breakpoint at the new location can produce amplicons 5c-3a and 5b-3c.

In various embodiments, gene fusions can be identified based on the presence of a fusion transcript, which can be detected by obtaining sequence information from transcribed mRNA.

Figure 5:
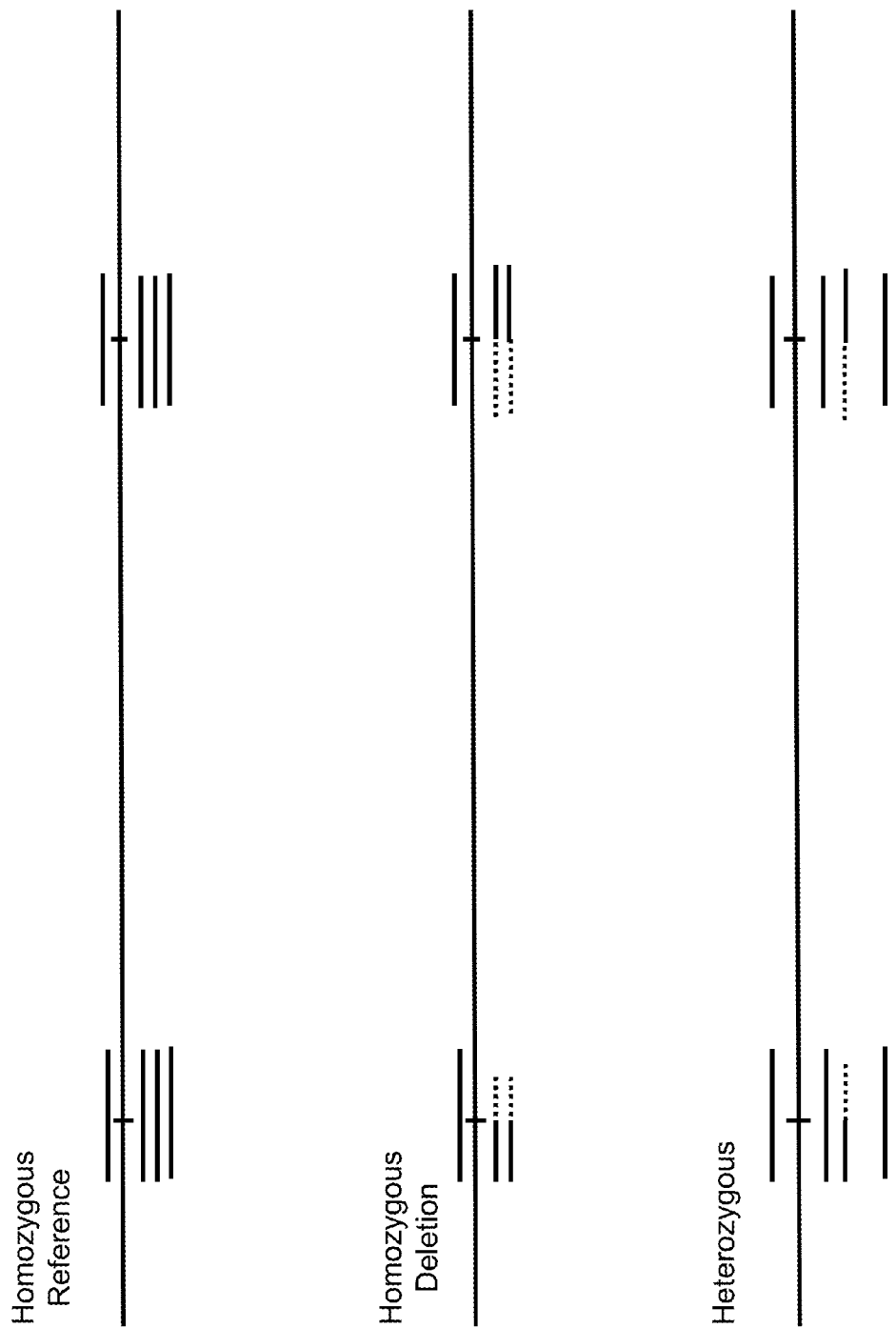
FIG. 5 is a diagram illustrating various deletion genotypes, in accordance with various embodiments.

FIG. 5 is a diagram showing the mapping of amplicons to the reference genome for various genotypes. In a Homozygous Reference genotype, all of the amplicons for the two breakpoint regions can present as fully mapped to the reference sequence. In a Homozygous Structural Variant genotype, all of the amplicons can present as partially mapped to the breakpoint regions outside of the structural variant. In a Heterozygous genotype, a first portion of the amplicons can present as partially mapped and second portion of the amplicons can present as fully mapped.

Figure 6:
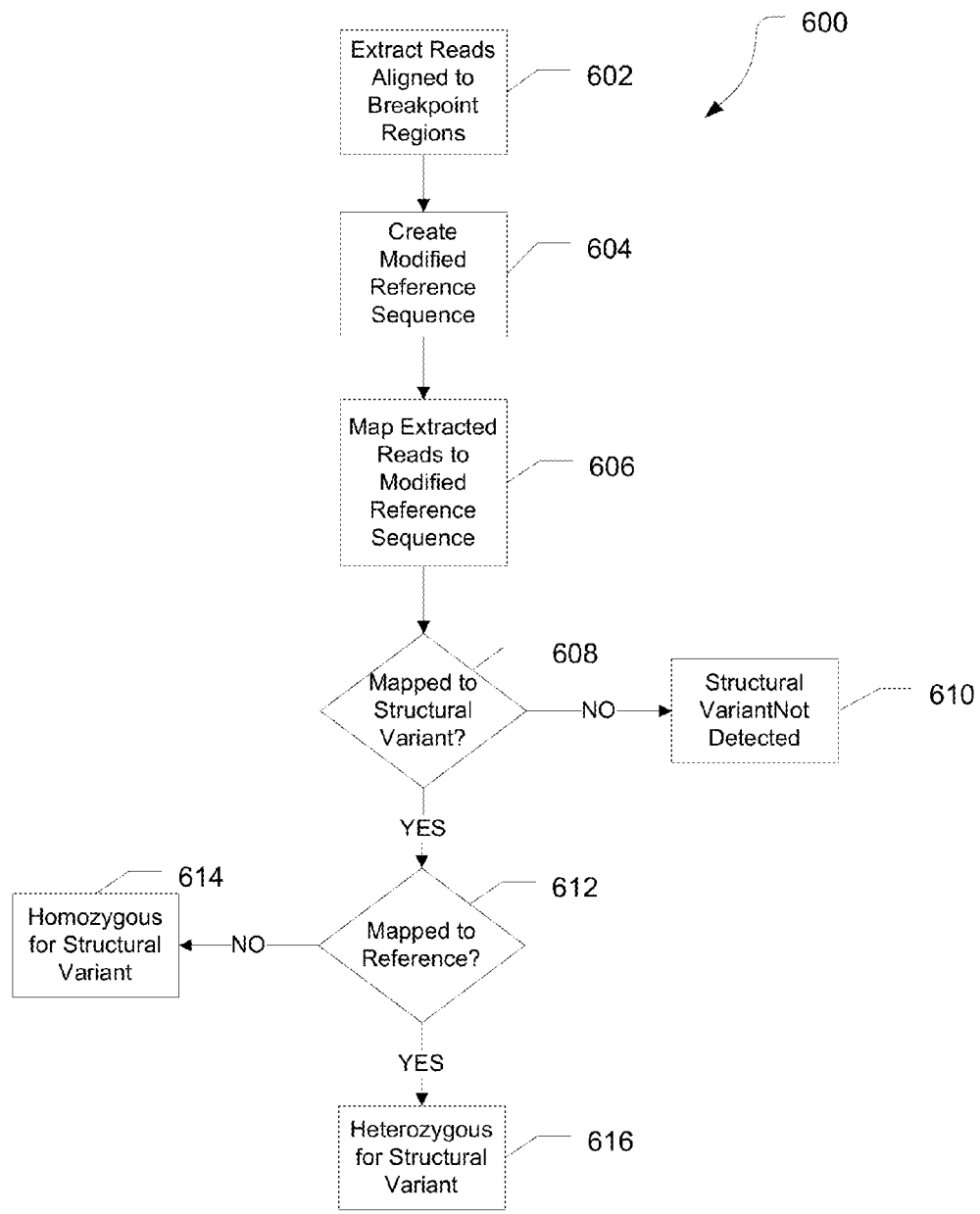
FIG. 6 is a flow diagram illustrating an exemplary method of detecting structural variants at known breakpoints, in accordance with various embodiments.

FIG. 6 is a flow diagram illustrating an exemplary method 600 of detecting structural variants at known breakpoints. At 602, reads that are aligned to the breakpoint region can be identified and extracted. The reads can include reads that are fully mapped to the breakpoint regions and reads that are partially mapped to the breakpoint regions. At 604, a modified reference sequence can be generated. The modified reference sequence can include a reference haplotype taken from the reference sequence and a putative structural variant haplotype generated by applying the suspected structural variant to the reference sequence. For example, a putative deletion haplotype can be generated by deleting the sequence information between the breakpoints or a putative inversion haplotype can be generated by inverting the sequence information between the breakpoints. At 606, the extracted reads can be aligned to the modified sequence.

At 608, the method can determine if reads are mapped to the structural variant haplotype. When reads are not mapped to the structural variant haplotype, a structural variant may not be detected, as illustrated at 610. Alternatively, when reads are mapped to the structural variant haplotype, the method can determine if reads are mapped to the reference haplotype, as illustrated at 612. When reads are not mapped to the reference haplotype, the nucleic acid sample can be identified as homozygous for the structural variant, as illustrated at 614. Alternatively, when reads are mapped to the reference haplotype, the nucleic acid sample can be identified as heterozygous for the structural variant, as illustrated at 616.

Figure 7:
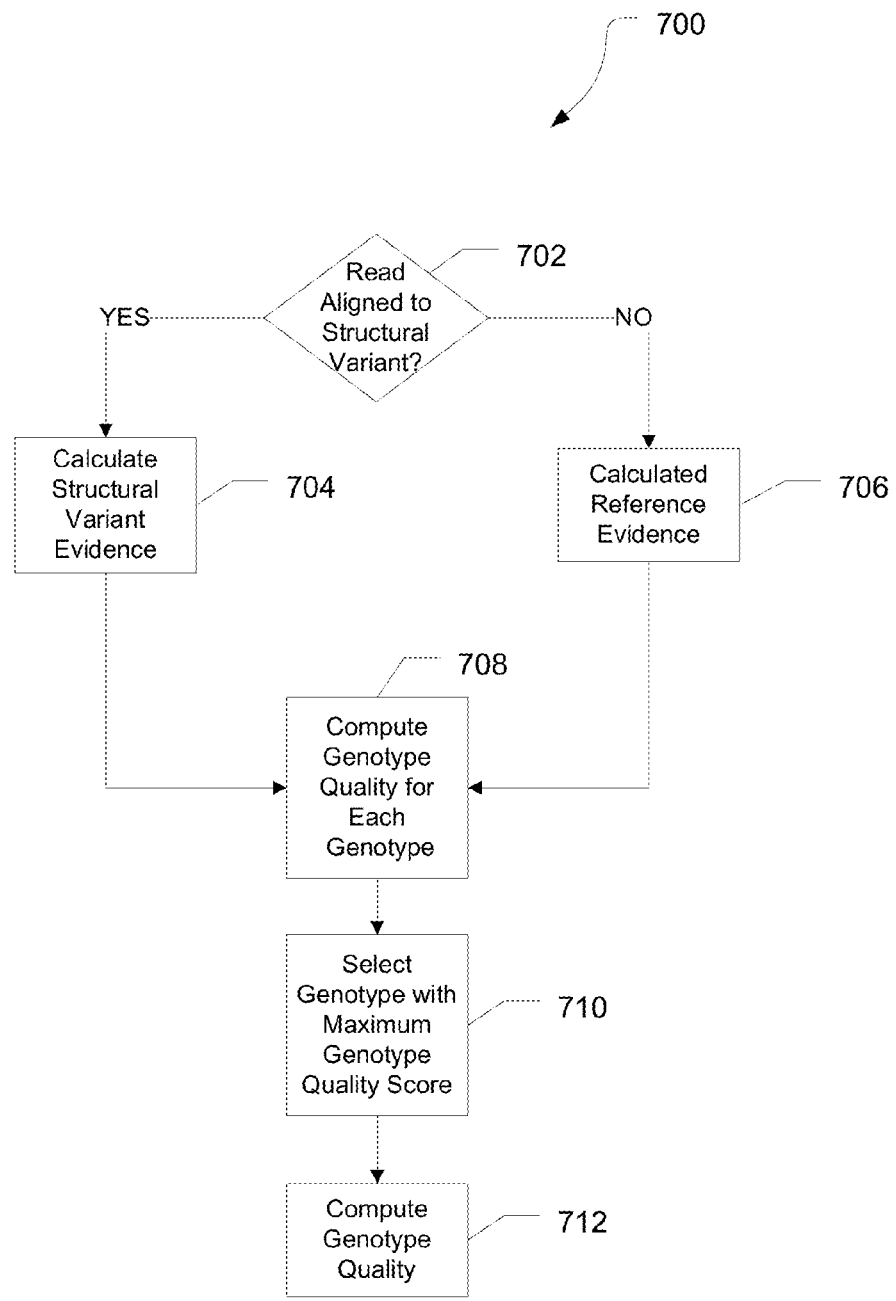
FIG. 7 is a flow diagram illustrating an exemplary method of calculating a variant score for a structural variant, in accordance with various embodiments.

FIG. 7 is a flow diagram illustrating an exemplary method 700 of calculating a quality score for a structural variant genotype. At 702, a determination can be made if a read aligns to the structural variant haplotype. When the read aligns to the structural variant haplotype, a structural variant evidence value can be calculated, as illustrated at 704. In various embodiments, the evidence can be calculated as:

$$\text{Evidence} = \text{Alignment Length}/\text{Read Length}$$

Alternatively, when the read maps to the reference haplotype, a reference evidence value can be calculated, as illustrated at 706. In various embodiments, the reference evidence value can be calculated as:

$$\text{Evidence} = 1 - \text{Alignment Length}/\text{Read Length}$$

At 708, a genotype quality score can be evaluated for each possible genotype: homozygous reference, homozygous structural variant, and heterozygous structural variant. In various embodiments, the genotype quality score can be calculated as:

$$P(G_j/\{E\}) = P(G_j) * P(\{E\}/G_j)/({}_{i=1}\Sigma^3(P(G_i)*P(\{E\}/G_i)))$$

where $P(G_j/\{E\})$ is the genotype quality score for genotype j, $P(G)$ is the probability of genotype j, $P(\{E\}/G_j)$ is calculated as ${}_{i=1}\Pi^n(P(e_i/G_j))$ where $P(e/G)$ is the normal probability distribution function of E with respect to G.

At 710, the genotype with the maximum genotype quality score can be selected as genotype supported by the evidence. At 712, the variant score can be calculated. In various embodiments, the variant score can be calculated as:

$$a = \log(P(E/G_m)) - \log(P(E/G_0))$$

In other embodiments, a genotype probability can be calculated for each of the possible genotypes (reference, heterozygous, homozygous variant) based on the reference probability.

$$P_{ref} = {}_{a=0.8}\Sigma^{1.0}(prob(a))/{}_{a=0}\Sigma^{1.0}(prob(a))$$

$$P_{het} = {}_{a=0.2}\Sigma^{0.8}(prob(a))/{}_{a=0}\Sigma^{1.0}(prob(a))$$

$$P_{hom} = {}_{a=0.0}\Sigma^{0.2}(prob(a))/{}_{a=0}\Sigma^{1.0}(prob(a))$$

where prob(a) can be the normal probability density function with a mean of E=R/T and standard deviation of S=E/sqrt (T), where T=R+V, R is the average of the number of reads mapped to each reference amplicon, and V is the average number of reads mapped to each variant amplicon. For example, when the structural variant is a deletion, R=(R1+R2)/2 and V=D. In another example, when the structural variant is an insertion, V=(I1+I2)/2.

The genotype call can be determined by taking the genotype with the maximum probability, the genotype quality can be the probability of the genotype call, and variant score can equal the genotype quality times ${}_{a=0}\Sigma^{1.0}$ (prob(a)).

In still other embodiments, the genotype probability can be calculated based on the variant probability.

$$P_{ref} = {}_{a=0.0}\Sigma^{0.2}(prob(a))/{}_{a=0}\Sigma^{1.0}(prob(a))$$

$$P_{het} = {}_{a=0.2}\Sigma^{0.8}(prob(a))/{}_{a=0}\Sigma^{1.0}(prob(a))$$

$$P_{hom} = {}_{a=0.8}\Sigma^{1.0}(prob(a))/{}_{a=0}\Sigma^{1.0}(prob(a))$$

where prob(a) can be the normal probability density function with a mean of E=V/T and standard deviation of S=E/sqrt (T). In particular embodiments where the variant is a deletion, V can be the number of reads that map to the deletion amplicon (D), and T=(C+D)/2 where C is the total number of reads that are extracted to be mapped to the modified reference genome. This way, it is not necessary to determine the number of reads that map to the reference amplicons.

Figure 8:
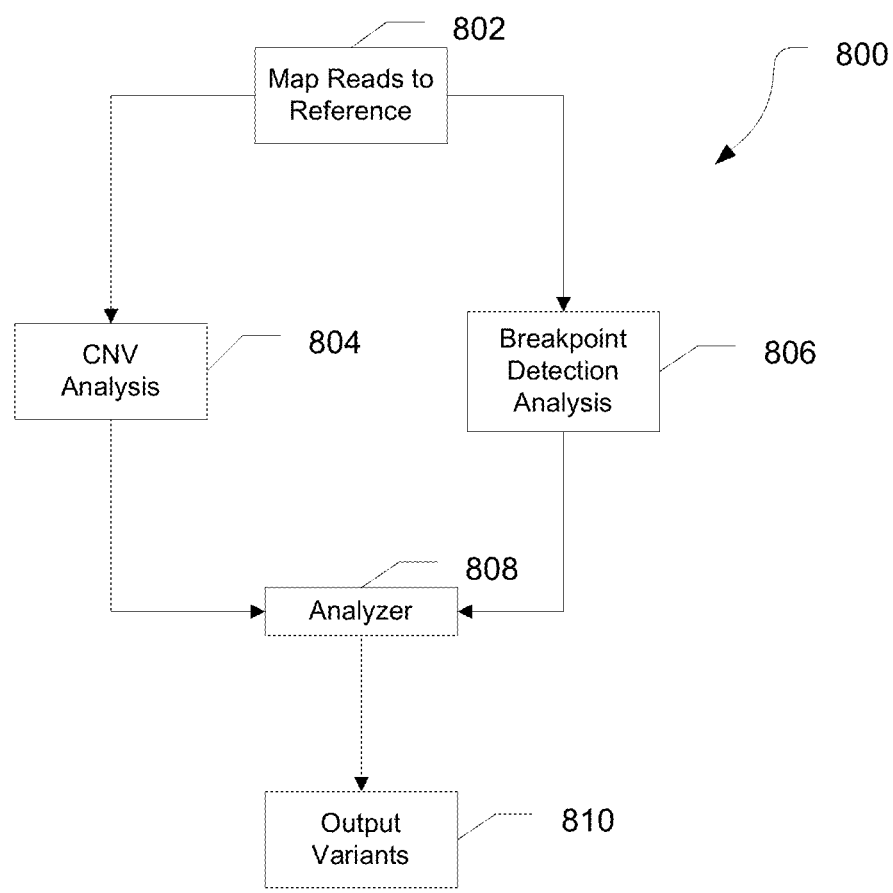
FIG. 8 is a flow diagram illustrating an exemplary method for identifying structural variants, in accordance with various embodiments.

FIG. 8 is a diagram illustrating an exemplary method for identifying structural variants. At 802, reads can be mapped to the reference sequence. At 804, a copy number variation analysis can be performed. In various embodiments, the reads can be used to determine coverage of various regions of the reference genome, and copy number variations can be identified based on differences in coverage of a region compared to an expected coverage. Exemplary methods of detecting copy number variations are described in U.S. Application No. 61/733,584, filed Mar. 6, 2013 and titled "SYSTEMS AND METHODS FOR DETERMINING COPY NUMBER VARIATION".

At 806, a breakpoint detection analysis can be performed. In various embodiments, the breakpoint detection analysis can be performed as previously described.

At 808, the results of the CNV analysis and the breakpoint detection analysis can be combined by the analyzer. In various embodiments, the analyzer can calculate a combined variant score. For example, the variant score from the CNV analysis can be added to the variant score of the breakpoint detection analysis.

At 810, the identified structural variants can be reported. In various embodiments, the variant score can be reported along with the structural variant. In various embodiments, when both the breakpoint detection analysis and the CNV analysis identify a structural variant, the variant can be identified with high confidence. In various embodiments, the breakpoint detection analysis can identify structural variants that can be undetectable by the CNV analysis. For example, an inversion or insertion may not be detectable by the CNV analysis. Further, depending on the resolution of the CNV analysis, deletions may be too small to be reliably connected by the CNV analysis. In another example, novel structural variants without known breakpoints may not be detectable by the breakpoint detection analysis.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD- RWs, magnetic tapes, and other optical and non-optical data storage devices. The computer readable medium can also be distributed over a network coupled computer systems so that the computer readable code is stored and executed in a distributed fashion.

In various embodiments, a method for detecting long deletions can include amplifying a nucleic acid sample in the presence of a primer pool to produce a plurality of amplicons, and sequencing the amplicons to generate a plurality of reads. The primer pool can includes a first and second pair of primers. The first pair of primers can includes a first and a second primer flanking a first breakpoint region and the second pair of primers can include a third primer and a forth primer flanking a second breakpoint region. The method can further include mapping the reads to a reference sequence; and detecting a structural variant between the first break point to the second breakpoint in the nucleic acid sample when a plurality of reads are partially mapped to regions of the reference genome between the first primer and the first breakpoint and between the second breakpoint and the fourth primer.

In particular embodiments, the first and second breakpoint regions can be exon boundaries.

In particular embodiments, the method can further include determining the nucleic acid sample is heterozygous for the deletion when a plurality of reads mapped to the regions of the reference genome between the first and second primers and between the third and fourth primers are present.

In particular embodiments, the method can further include determining the nucleic acid sample is homozygous for the deletion when reads mapped to the regions of the reference genome between the first and second primers and between the third and fourth primers are not present.

In particular embodiments, the primer pool can further include at least one primer pair within the region between the first and second breakpoints. The method can further include determining the nucleic acid sample is heterozygous when a plurality of reads mapped to the region between the first and second breakpoints are present. Alternatively, the method can further include determining the nucleic acid sample is homozygous when a plurality of reads mapped to the region between the first and second breakpoints are not present.

In various embodiments, a method of detecting structural variants can include amplifying a nucleic acid sample in the presence of a primer pool to produce a plurality of amplicons, and sequencing the amplicons to generate a plurality of reads. The primer pool can include a first and second pair of primers. The first pair of primers can include a first and a second primer flanking a first breakpoint region, and the second pair of primers can include a third primer and a forth primer flanking a second breakpoint region. The method can further include mapping the reads to a reference sequence including a full length allele and a truncated allele with a deletion between the first and second breakpoints, and detecting a deletion between the first break point to the second breakpoint in the nucleic acid sample when a plurality of reads are mapped to the truncated allele are present.

In particular embodiments, the first and second breakpoint regions can be exon boundaries.

In particular embodiments, the plurality of reads mapped to the truncated allele can result from amplification of the nucleic acid sample with the first and fourth primers.

In particular embodiments, the method can further include determining the nucleic acid sample is heterozygous for the deletion when a plurality of reads mapped to the full length allele are present. The reads mapped to the full length allele can be the product of amplification of the nucleic acid sample with the first and second primers and with the third and fourth primers.

In particular embodiments, the method can further include determining the nucleic acid sample is homozygous for the deletion when a plurality of reads mapped to the full length allele are not present.

In particular embodiments, the primer pool can further include at least one primer pair within the region between the first and second breakpoints. The method can further include determining the nucleic acid sample is heterozygous when a plurality of reads mapped to the region between the first and second breakpoints are present, or determining the nucleic acid sample is homozygous when a plurality of reads mapped to the region between the first and second breakpoints are not present.

In various embodiments, a method for detecting long deletions can include amplifying a nucleic acid sample in the presence of a primer pool to produce a plurality of amplicons, the primer pool including first and second primers, and sequencing the amplicons to generate a plurality of reads. The first primer can correspond to a first breakpoint region, and the second primer can correspond to a second breakpoint region. The method can further include mapping the reads to a reference sequence including a reference allele and a structural variant allele with a structural variant between the first and second breakpoint regions, and detecting a structural variant between the first breakpoint region to the second breakpoint region in the nucleic acid sample when a plurality of reads are mapped to the structural variant allele are present.

In particular embodiments, the first and second breakpoint regions are exon boundaries.

In particular embodiments, the primer pool can further include at least one primer pair within the region between the first and second breakpoints. The method can further include determining the nucleic acid sample is heterozygous when a plurality of reads mapped to the region between the first and second breakpoints are present or determining the nucleic acid sample is homozygous when a plurality of reads mapped to the region between the first and second breakpoints are not present.

What is claimed is:

1. A method for detecting a structural variant comprising:
   amplifying a nucleic acid sample in the presence of a primer pool to produce a plurality of amplicons, the primer pool including first and second pairs of primers, the first pair of primers including a first and a second primer flanking a first breakpoint region associated with a first breakpoint, the second pair of primers including a third primer and a fourth primer flanking a second breakpoint region associated with a second breakpoint;
   sequencing the amplicons to generate a plurality of reads;
   mapping the reads to a reference sequence, the reference sequence including a whole or partial genome; and
   detecting the structural variant between the first breakpoint and the second breakpoint in the nucleic acid sample when a first portion of the plurality of reads is partially mapped to first and second regions of the reference genome, wherein the first region is between the first primer and the first breakpoint and wherein the second region is between the second breakpoint and the fourth primer.

2. The method of claim 1, wherein the first and second breakpoint regions are exon boundaries.

3. The method of claim 1, further comprising determining the nucleic acid sample is heterozygous for the structural variant when a second portion of the plurality of reads is mapped to regions of the reference genome between the first breakpoint and the second primer and between the third primer and the second breakpoint.

4. The method of claim 1, further comprising determining the nucleic acid sample is homozygous for the structural variant when reads mapped to regions of the reference genome between the first breakpoint and the second primer and between the third primer and the second breakpoint are not present.

5. The method of claim 1, wherein the primer pool further comprises at least one primer pair within a region between the first and second breakpoints.

6. The method of claim 5, further comprising determining the nucleic acid sample is heterozygous when a second portion of the plurality of reads is mapped to the region between the first and second breakpoints.

7. The method of claim 5, further comprising determining the nucleic acid sample is homozygous when reads mapped to the region between the first and second breakpoints are not present.

8. A method of detecting a deletion comprising:
amplifying a nucleic acid sample in the presence of a primer pool to produce a plurality of amplicons, the primer pool including first and second pairs of primers, the first pair of primers including a first and a second primer flanking a first breakpoint region associated with a first breakpoint, the second pair of primers including a third primer and a fourth primer flanking a second breakpoint region associated with a second breakpoint;
sequencing the amplicons to generate a plurality of reads;
mapping the reads to a reference sequence, the reference sequence including a full length allele and a truncated allele with a deletion between the first and second breakpoints; and
detecting the deletion between the first breakpoint and the second breakpoint in the nucleic acid sample when a first portion of the plurality of reads is fully mapped to the truncated allele, but only partially mapped to the full length allele.

9. The method of claim 8, wherein the first and second breakpoint regions are exon boundaries.

10. The method of claim 8, wherein the first portion of the plurality of reads mapped to the truncated allele correspond to the amplicons resulting from amplification of the nucleic acid sample with the first and fourth primers.

11. The method of claim 8, further comprising determining the nucleic acid sample is heterozygous for the deletion when a second portion of the plurality of reads is mapped to the full length allele between the first breakpoint and the second primer and between the third primer and the second breakpoint, wherein the reads in the second portion correspond to the amplicons resulting from amplification of the nucleic acid sample with the first and second primers and with the third and fourth primers.

12. The method of claim 8, further comprising determining the nucleic acid sample is homozygous for the deletion when reads mapped to the full length allele between the first breakpoint and the second primer and between the third primer and the second breakpoint are not present.

13. The method of claim 8, wherein the primer pool further comprises at least one primer pair within a region between the first and second breakpoints.

14. The method of claim 13, further comprising determining the nucleic acid sample is heterozygous when a second portion of the plurality of reads is mapped to the region between the first and second breakpoints.

15. The method of claim 13, further comprising determining the nucleic acid sample is homozygous when reads mapped to the region between the first and second breakpoints are not present.

* * * * *